United States Patent
Epley

(10) Patent No.: US 7,351,246 B2
(45) Date of Patent: Apr. 1, 2008

(54) MINIMALLY INVASIVE, SUSTAINED, INTRA-TYMPANIC DRUG DELIVERY SYSTEM

(76) Inventor: John M. Epley, 545 NE. 47th Ave., Suite 212, Portland, OR (US) 97213

( * ) Notice: Subject to any disclaimer, the term of this patent is extended or adjusted under 35 U.S.C. 154(b) by 128 days.

(21) Appl. No.: 11/039,556

(22) Filed: Jan. 20, 2005

(65) Prior Publication Data

US 2005/0182385 A1 Aug. 18, 2005

Related U.S. Application Data

(60) Provisional application No. 60/538,077, filed on Jan. 20, 2004.

(51) Int. Cl.
*A61M 31/00* (2006.01)
*A61F 11/00* (2006.01)
(52) U.S. Cl. .................... 606/109; 604/275; 604/35
(58) Field of Classification Search ............... 604/21, 604/35, 239, 275, 514; 606/109
See application file for complete search history.

(56) References Cited

U.S. PATENT DOCUMENTS

| | | | |
|---|---|---|---|
| 3,645,268 A * | 2/1972 | Capote | ............ 604/117 |
| 4,034,759 A | 7/1977 | Haerr | |
| 4,334,538 A * | 6/1982 | Juhn | ............ 604/35 |
| 5,405,321 A * | 4/1995 | Reeves | ............ 604/44 |
| 5,421,818 A | 6/1995 | Arenburg | |
| 5,476,446 A | 12/1995 | Arenburg | |
| 5,747,529 A | 5/1998 | Gordaliza et al. | |
| 6,120,484 A | 9/2000 | Silverstein | |
| 6,368,315 B1 | 4/2002 | Gillis et al. | |
| 6,377,849 B1 * | 4/2002 | Lenarz et al. | ............ 604/21 |
| 6,440,102 B1 | 8/2002 | Arenburg et al. | |
| 6,648,873 B2 * | 11/2003 | Arenberg et al. | ............ 604/509 |
| 6,685,697 B1 | 2/2004 | Arenburg et al. | |
| 6,770,080 B2 * | 8/2004 | Kaplan et al. | ............ 606/109 |
| 7,044,962 B2 * | 5/2006 | Elliott | ............ 623/1.13 |
| 2004/0097839 A1 * | 5/2004 | Epley | ............ 600/595 |
| 2007/0167918 A1 * | 7/2007 | Reed et al. | ............ 604/187 |

OTHER PUBLICATIONS

Wearne et al., "Control of Spatial Orientation of the Angular Vistibulocular Reflex by the Nodulus and Uvula", J. Neurophysiol. 79:2690-2715 (1998).

* cited by examiner

*Primary Examiner*—Kevin C. Sirmons
*Assistant Examiner*—Andrew Gilbert
(74) *Attorney, Agent, or Firm*—Ater Wynne LLP

(57) ABSTRACT

A convenient and preferably wearable system and method for implementing the controlled and sustained delivery of a medical liquid through the tympanic membrane and into the middle ear including port structure that produces a minimal opening in the membrane, a wearable and fixated fluid-conduit structure coupleable to the port structure, a reservoir adapted to contain delivery fluid, and an operationally controllable pump system applied to the fluid conduit structure, and/or an iontophoretic electrode system applied within the fluid conduit structure and to the subject's body, and operable to effect the delivery of reservoir-held fluid or medically active ions through the fluid conduit and port structures to the middle ear.

15 Claims, 9 Drawing Sheets

MINIMALLY INVASIVE, SUSTAINED, INTRA-TYMPANIC DRUG DELIVERY SYSTEM

CROSS-REFERENCE TO RELATED APPLICATION

This application claims benefit of U.S. Provisional Application 60/538,077, filed Jan. 20, 2004, which is incorporated herein by reference in its entirety.

BACKGROUND OF THE INVENTION

This invention relates to an apparatus and method for the sustained, selectively controlled and metered introduction of a medical fluid, such as a drug, through the tympanic membrane and into the middle ear of a patient.

It is desirable in certain circumstances to administer medications or other medical fluids into the middle ear through the tympanic membrane, and thence to the inner ear. Intratympanic perfusion of drugs for treatment of inner ear conditions was popularized the 1970's in Europe with the treatment of Meniere's disease with intratympanic aminoglycoside antibiotics. This route of administration has since gained wider utilization in the treatment of many other ear conditions as well, including tinnitus, sudden hearing loss, and various forms of labyrinthine dysfunction. Medications typically used include aminoglycosides, corticosteroids and local anesthetics. Anticipated delivery of other medications by this route has undergone widespread discussion.

Intratympanic delivery of drugs has been accomplished in the past principally by making a small incision in the anesthetized tympanic membrane (ear drum), inserting a needle or catheter into the middle ear, infusing the drug in liquid form and allowing it to be absorbed into the inner ear, probably mainly by way of the round window membrane. Other methods have included placing an incision or implanted tube in the tympanic membrane and then having the patient self-dispense the drug into the external ear canal whereby it is intended to pass through the opening into the middle ear, and thence the inner ear. This has the disadvantage that infectious debris can be carried into the middle ear from the external canal, with the risk of creating a middle ear infection, and passage of the liquid drug into the middle ear is inhibited by the surface tension of the liquid. These problems have been partially solved by inserting a wick between the external ear canal and the middle ear, as in U.S. Pat. No. 6,120,484 to Silverstein. But this method has the disadvantages of possible patient noncompliance, errors in following directions, confusion of medications, failure of some or all of the instilled drops to reach or pass through the wick and chronic perforations due to the extended use of the wick.

U.S. Pat. No. 5,474,529 to Arenburg describes a multi-functional inner ear treatment and diagnostic system, using a two channel catheter that leads to a small reservoir placed in the round window niche of the middle ear and open to the round window membrane via small openings through which the drug is allowed to diffuse. Implantation is difficult, usually requiring a hospital operation, and the large catheter often leaves a defect in the tympanic membrane. Round window membrane erosion is a risk due to prolonged contact with the implanted structure.

Other examples of apparatus and methods for accomplishing intratympanic drug delivery are described, for example, in U.S. Pat. Nos. 4,034,759, 5,421,818, 5,474,529, 5,476,446, 6368,315, 6,440,102 and 6,685,697.

Recent studies have shown that there is a blood-labyrinth barrier similar to the blood-brain barrier, such that very little of most medications delivered systemically (oral, IV, etc.) is transported to the inner ear. Thus, to accomplish a therapeutic concentration of the medication within the inner ear when delivered via the systemic route, high concentrations of the medication over sustained periods of time are necessary, increasing the risk of systemic side effects.

On the other hand, if a solution containing the drug molecules is placed into the middle ear and is allowed to remain for a period of time, a small portion of the molecules will be absorbed into the inner ear, probably mainly by diffusion through the round window membrane. The amount of absorption of the drug molecules through the round window, and hence the dose of the drug reaching the inner ear structures, is proportional to the concentration of the drug in contact with the round window membrane, and the time the drug remains in contact with the round window membrane at said concentration.

The middle ear cavity can hold approximately 0.5 cc of fluid. Its outer surface is lined by a mucous membrane, which absorbs medication molecules from the middle ear. If a solution (perfusate) containing medication is thus placed in the middle ear cavity, the molecules of that medication in the solution will diffuse over time into the surrounding tissues, including the round window membrane. The round window represents only a small proportion (less than 2%) of surface area of the surrounding tissues. Therefore only a small portion of the molecules of drug will diffuse through the round window into the inner ear. On the other hand, the volume of the inner ear is only about 1 cc, so that relatively few molecules of medication are needed to obtain a therapeutic concentration in the inner ear. Molecules of drug diffuse out of the solution into the surrounding tissues so that concentration of drug in the solution becomes less with time, following an asymptotic curve. The applicant's studies indicate that the half-life of drug molecules (i.e., time until one-half of the quantity of drug is depleted) in the solution in the middle ear is approximately 5 minutes. Thus, if the typical protocol for single injection is followed, and 0.5 cc of a drug is infused into the middle ear and allowed to remain for 30 minutes, the concentration of the drug in the middle ear becomes quite low and thus ineffective, during last 15-20 minutes.

What is presented in this invention is an apparatus that is easily used, is capable of controlled administration of fluids into the ear, is stable and comfortable, and which is easily inserted and removed with minimal effect on the structures of the ear.

SUMMARY OF THE INVENTION

Figure 1:
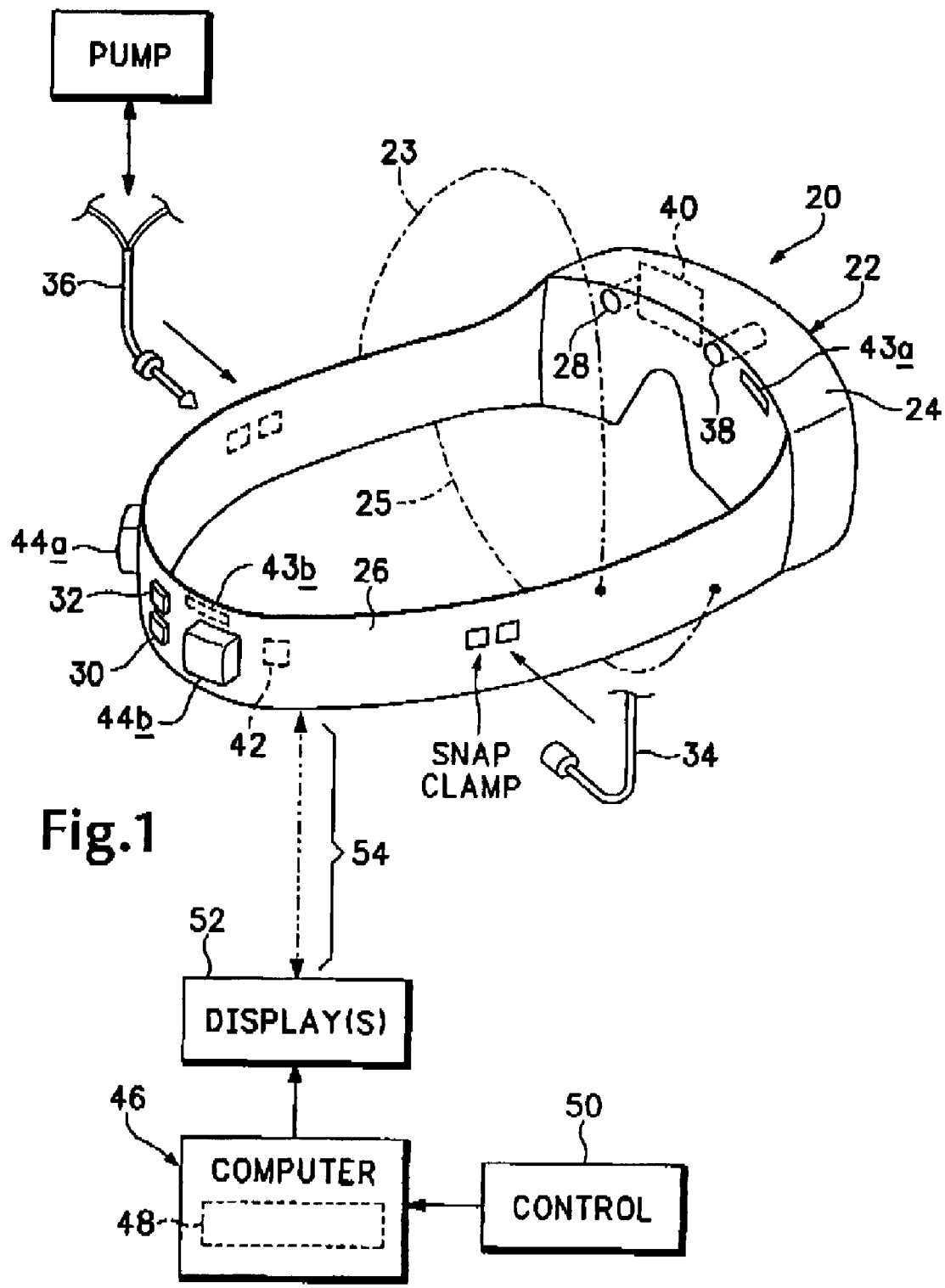
FIG. 1 is an isometric view of a stabilizing headgear of an aspect of the invention.

This invention is an intra-tympanic perfusion apparatus comprising
a) a needle having a sharpened end adapted to pierce the tympanic membrane of an ear and a distal end, the needle having at least one longitudinal bore having a fluid outlet proximate to the sharpened end for delivering fluid to or removing fluid from the middle ear through the needle and a fluid inlet proximate to the distal end;
b) a flexible lumen being in fluid communication with the fluid inlet proximate to the distal end of the needle;
c) means for delivering a controllable amount of a fluid into the middle ear through the flexible lumen and the needle; and
d) means for removing fluids from the middle ear through needle.

In another aspect, this invention is an intra-tympanic apparatus comprising
a) a needle having a sharpened end adapted to pierce the tympanic membrane of an ear and a distal end, the needle having at least one longitudinal bore having a fluid outlet proximate to the sharpened end for delivering fluid to or removing fluid from the middle ear through the needle and a fluid inlet proximate to the distal end;
b) a flexible lumen being in fluid communication with the fluid inlet proximate to the distal end of the needle,
wherein the sharpened end of the needle is adapted to form multiple connected incisions in the tympanic membrane that extend radially from a central point to form multiple flaps in the tympanic membrane.

This invention is also a process for delivering fluid to or removing fluid from the middle ear, comprising
a) puncturing a tympanic membrane of an ear with a needle having a sharpened end adapted to pierce the tympanic membrane and a distal end, wherein
1) the needle has at least one longitudinal bore having a fluid outlet proximate to the sharpened end for delivering fluid to or removing fluid from the middle ear and a fluid inlet proximate to the distal end; and
2) a flexible lumen is in fluid communication with the fluid inlet proximate to the distal end of the needle;
b) securing the needle in place such that the sharpened end and the fluid outlet extend into the middle ear and at least a portion of the flexible lumen extends outwardly from the tympanic membrane; and
c) delivering at least one fluid to or removing at least one fluid from the middle ear through the fluid outlet of the needle.

The present invention represents a significant and substantial advance in middle and inner ear treatment. Use of the invention enables a multiplicity of therapeutic measures to be readily accomplished using an undemanding design of components and minimally invasive surgical procedures. Specifically, the various embodiments of the invention set forth herein enable:

(1) the delivery of vestibulo-active, cochleo-active and osmotically-active liquid therapeutic agents via the middle ear to the inner ear structures;

(2) the controlled, relatively clog-free, active and passive withdrawal of fluids of intrinsic and extrinsic origin from the middle ear space, (3) maximal dose available continuously to the inner ear within a short period of time, so as to provide complete treatment in-office, (4) minimization of systemic side effects by limiting systemic absorption of therapeutic medication beyond the ear structures, (5) avoidance of direct contact of components with inner ear structures and thus less risk of damaging the inner ear structures, (6) enhanced absorption and/or diffusion into the inner ear of medication through iontophoretic application, (7) the use of an alternating push-pull method to evacuate and replenish the medically active molecules, thus allowing use of a single-bore port structure, (8) delivery of therapeutic agents to middle ear structures, and (9) easy, fast and minimally-invasive insertion and removal of components in a simple setting.

An opening to the middle ear is created in the tympanic membrane, and a liquid-passage port structure is established in this opening. This can typically performed using only local anesthesia. The port structure can possess any suitable configuration, and may be either permanently, or only temporarily, installable.

A fluid conduit structure is appropriately coupled disconnectably to the port structure, and is connected, at a location which is upstream from the port structure relative to the membrane, to a small selectively controllable metering pump. This pump in turn, is connected to a suitable reservoir containing the liquid substance which is to be introduced into the middle ear.

The fluid conduit structure, the pump, and the reservoir are small, are comfortably wearable by a patient, and may be located:

(a) external to the ear, and effectively "hung", or mounted, on the ear, "hearing-aid" style;

(b) external to the ear and mounted on stabilizing headgear; or (c) entirely as a miniaturized assembly within the ear, per se.

Liquid delivery may be controlled in any suitable fashion, as by:

(a) controlled-flow steady stream;

(b) pulsed delivery in accordance with a selectable pulse "pattern"; or (c) manually.

Computer control structure, greatly minimized, and preferably programmable, may be included for flow-control purposes.

In another aspect, the drug is delivered by iontophoresis using internally oriented electrodes to induce the flow of medically active ions through the device and to the ear structures. A preferred embodiment of the invention makes use of multiple stages of charged electrodes to mobilize the medically active ions toward the port structure and thence to the ear structures. These longitudinal stages are suitably arranged longitudinally along the length of a fluid conduit that delivers the ions into the middle ear through the tympanic membrane.

DETAILED DESCRIPTION OF THE INVENTION

Figure 2:
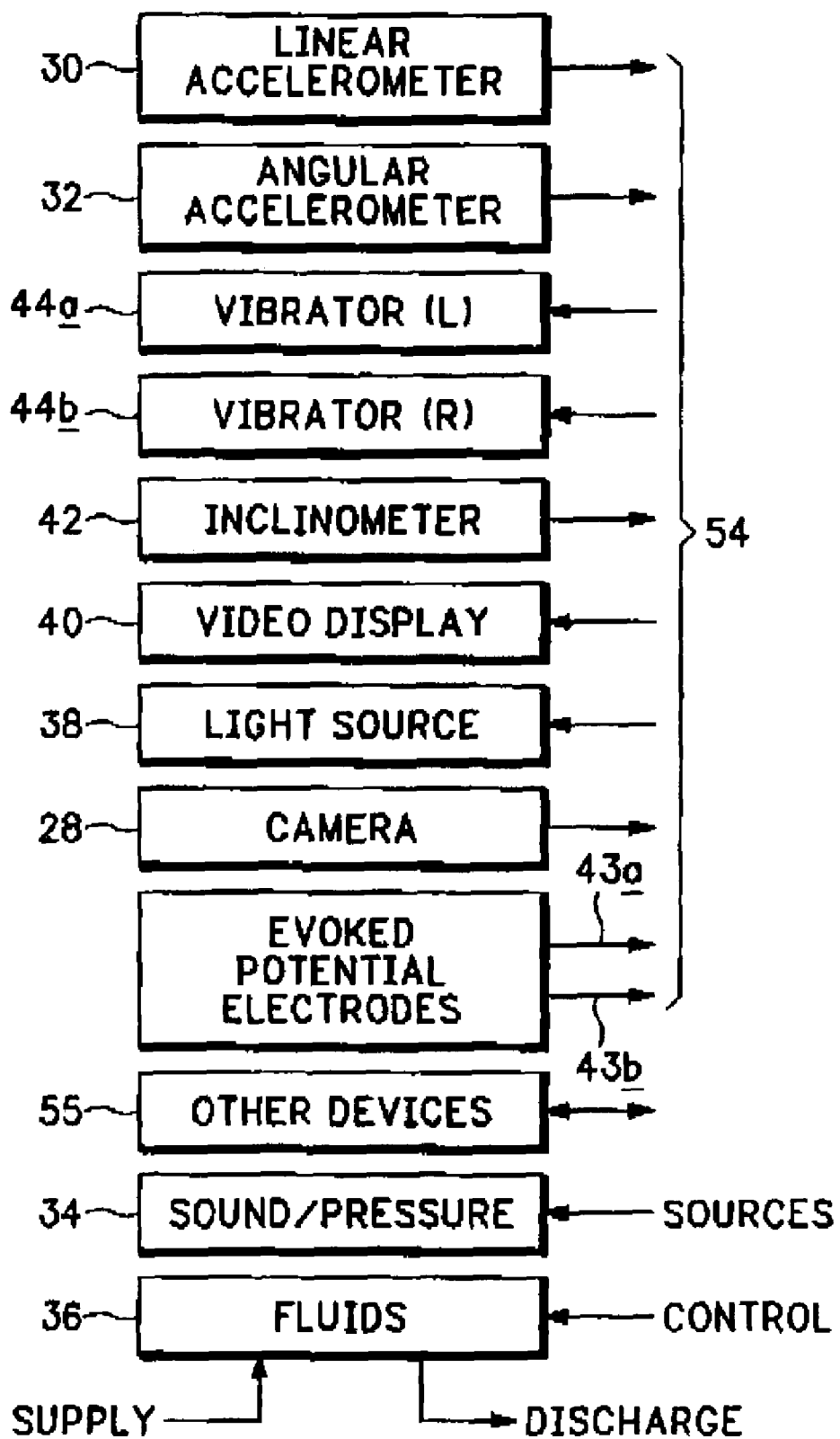
FIG. 2 is a flow chart identifying optional features of the invention.

Turning now to the drawings, and beginning first with reference to FIGS. 1 and 2, indicated generally at 20 in FIG. 1 is one form, and collection, of apparatus constructed and useable in accordance with a preferred implementation of, and manner of practicing, in a best-known mode, the present invention. Apparatus 20, as illustrated in FIG. 1, takes the form of a goggle-like frame structure 22 .which includes an eye-bridging housing structure, or housing 24, and a head-wrap band 26 which extends from housing 24 in a loop that enables the frame structure to be secured appropriately, in a goggle-wearing fashion, to and around a human subject's head. Band 26 is preferably length-adjustable (in any suitable manner which is not specifically illustrated herein) to enable appropriate and comfortable tightening around the head, is preferably formed of a relatively configurationally stable plastic material, such as a medical-grade polycarbonate material, and may have all, or a portion, of its inner surface equipped appropriately, if so desired, with any suitable high-friction material, such as silicone rubber. Whether or not such a friction material is employed is completely a matter of choice, it only being important, in accordance with the structure and practice of this invention, that when this frame structure is "installed" in a secured condition on a subject's head, it will effectively occupy a condition thereon of substantially complete stability with respect to no relative motion being permitted between the frame structure and the head under normal subject head-motion conditions.

While frame structure 22 is shown as simply involving the two components specifically illustrated and mentioned, it can clearly be modified, if so desired, with other stabilization features, such as an additional strap which might have opposite ends joined to band 26 to extend adjustably and tightenably over the crown of the head, as suggested by dash-dot line 23. It might further include, also if so desired, additional stabilization provided by something in the nature of a conventional, tightenable and adjustable under-the-chin strap, as suggested by dash-dot line 25, and by the previously mentioned ear canal insert.

As has been mentioned earlier herein, practice of an embodiment of the present invention contemplates the selective simultaneous use of plural (at least two at a given time) devices, appropriately anchored to frame structure 22 for the purpose of either collecting data from a subject relative to vestibular behavior (sensors), and/or delivering stimuli to a subject (stimuli deliverers). A representative (but non-exhaustive) list of such devices is now presented, and each of these different kinds of devices is illustrated just very simply and schematically in FIG. 1 in place at a representative selected location on structure 22. Thus, the illustrated devices include a small infrared video camera, or electronic video-image collecting device, 28 which is suitably positioned inside housing 24, a three-axis linear accelerometer 30, a three-axis angular accelerometer 32, a combined sound deliverer and air-pressure modifier 34 (stimuli deliverers), a device 36, referred to herein as fluid-flow structure, for delivering selected fluids/liquids to the ear (also a stimulus deliverer), a suitable, selected light source, or light-emitting structure, 38 which is also mounted inside of housing 24, a small video screen, or visual image-presenting structure, 40 which is disposed within housing 24, an inclinometer 42, a pair of spaced evoked-potential electrodes 43a, 43b, and two (left and right) vibration-generating structures, or vibrators, 44a, 44b, respectively (also referred to as stimuli deliverers).

Fragmentarily illustrated fluid-flow structure 36, only one of which is shown in FIG. 1, could be used in combination with a second such device on the opposite side of band 26, thus to deliver stimuli and/or treatment fluids (liquids) selectively to both ears if desired.

Further with respect to devices 34, 36, while these particular kinds of devices may take a number of different forms, certain preferred, specific constructions for these devices have been found to work especially well in the environment of the present invention, and these specific constructions are illustrated and described herein also, and are specifically discussed a bit later in this text.

At the bottom of FIG. 2 there is a block which is labeled FLUIDS, and this represents a source and return reservoir of fluids supplied to and drawn away from, as appropriate, device 36 when that device is being employed as a fluid-flow structure. A single-headed arrow pointing into the right side of this block, labeled CONTROL, reflects a connection through the communication structure to computer 46, whereby this computer, monitoring nystagmus behavior in a subject, is enabled to control the delivery of fluids, for example, to one of a subject's ears via device 36.

Figure 3:
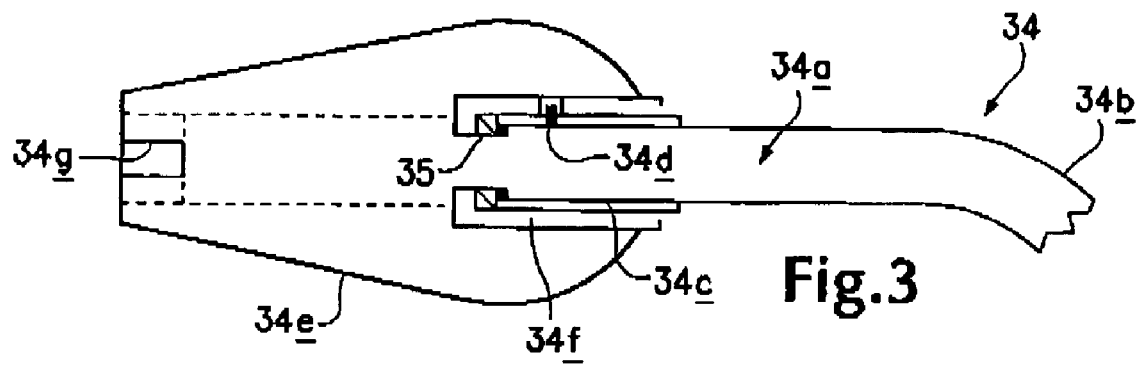
FIG. 3 is a side view, in section, of a combined sound deliverer and air-pressure modifier device.
Figure 3A:
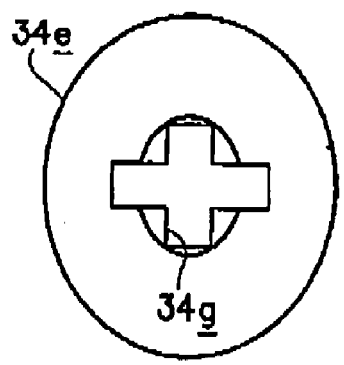
FIG. 3A is an enlarged end view of a tip for a combined sound deliverer and air-pressure modifier device as shown in FIG. 3.

As was mentioned earlier, I have found that there are certain specific structures for devices 34, 36 which work especially well in the headgear-apparatus setting of the present invention. FIGS. 2, 3 and 3A illustrate a preferred construction for a combined sound deliverer and air-pressure modifier device, such as device 34.

Combined device 34 includes an elongate, ovoid body structure 34a, which may be furnished with a generally right angle bend as is shown at 34b, and which may be made of a relatively rigid plastic material, with this ovoid body including what is referred to herein as a delivery end 34c inwardly from which there is provided an outwardly projecting nubbin 34d. Fitted removeably and replaceably on this outer body end is a soft and pliable, typically rubber-like oblong and tapered bulb 34e which is fitted with a mounting structure 34f that enables removable, nubbin-locked positioning of the bulb on body end 34c. Bulb includes an outer exposed end possessing a cross-shaped non-occluding fluid-passage aperture 34g. A washer 35 provides sealing engagement between bulb 34e and body end 34c.

The non-illustrated end of ovoid body 34a, during use of this device, is suitably coupled to a source of selected sound, or to a source which enables plus and minus varying of air-pressure under circumstances with body end 34c and bulb 34e suitably inserted into a subject's ear. The soft and pliable nature of bulb 34e, when engaged with ear tissue, produces effectively a fluid tight seal with this tissue which enables the development of pressures both above and below atmospheric pressure. It also provides a relatively good acoustical seal against the introduction of extraneous noise to the ear under circumstances where it is intended that a specific sound be delivered to the ear or ears.

Figure 4:
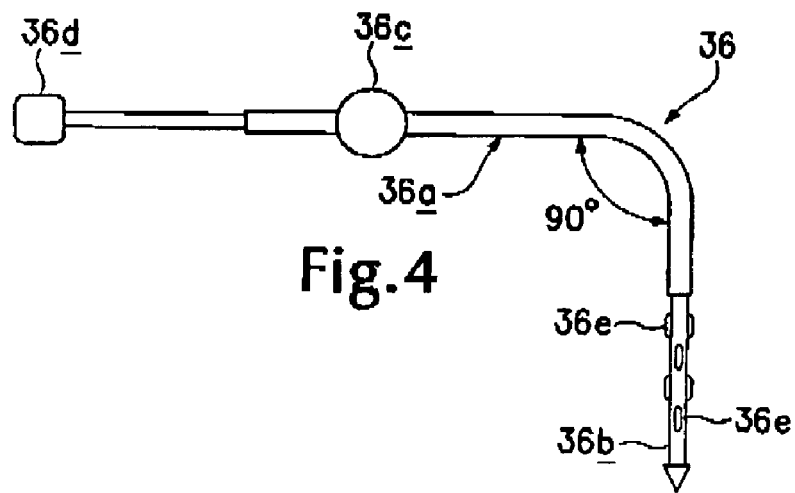
FIG. 4 is a side view of an intra-tympanic apparatus of one embodiment of the invention.
Figure 5:
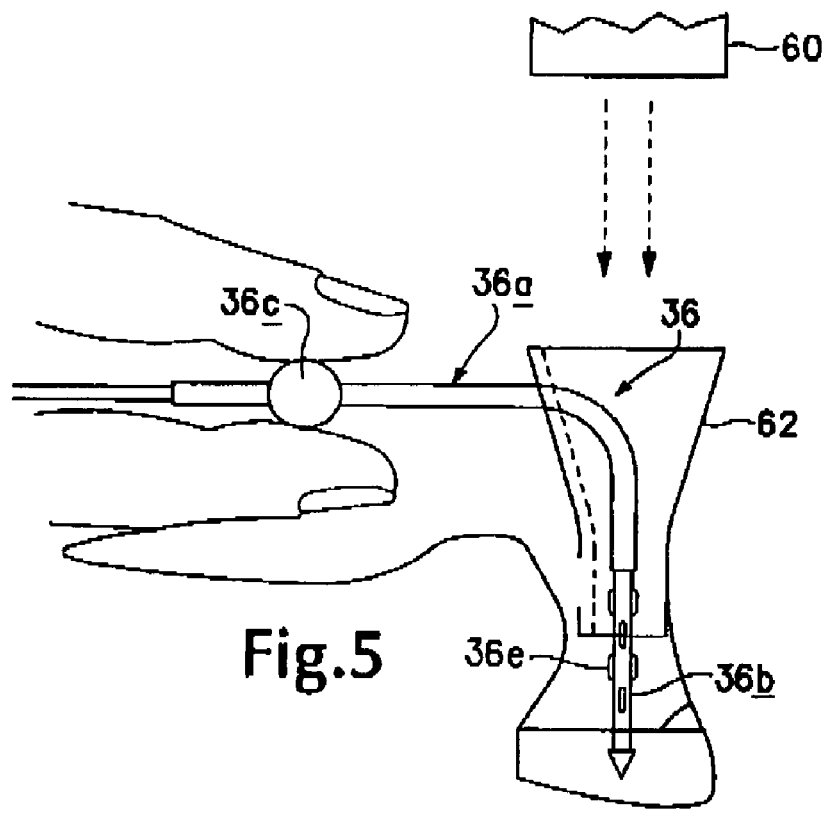
FIG. 5 is a side view, partially in section, illustrating the placement and use of an embodiment of the invention.
Figure 6:
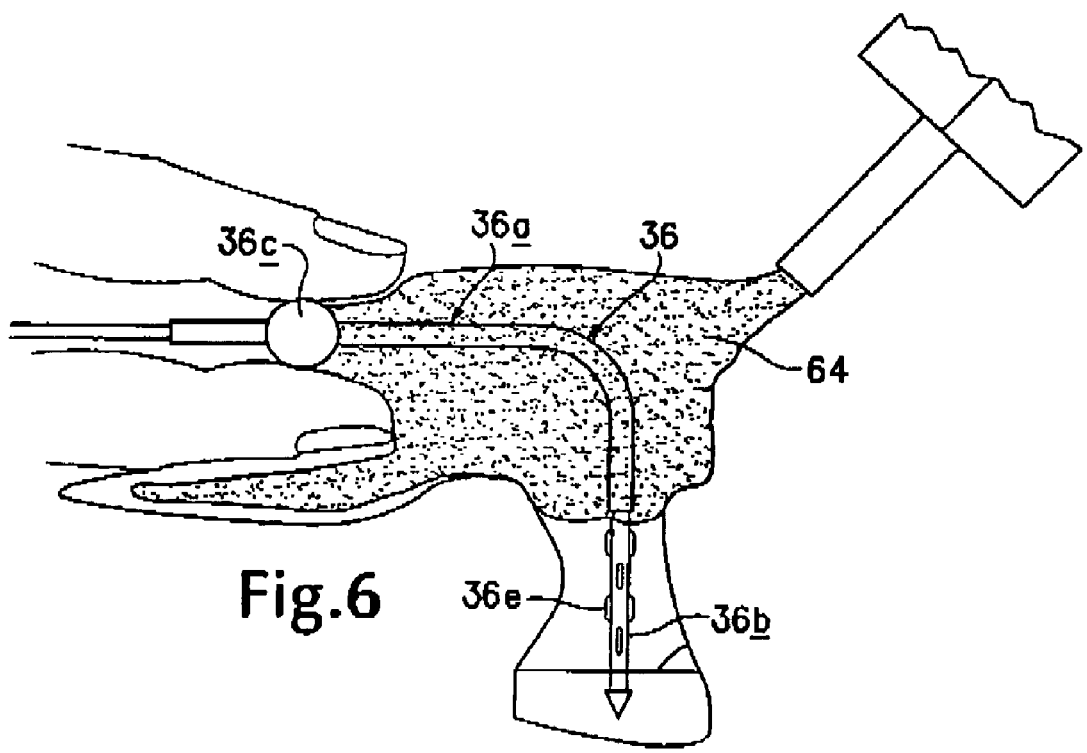
FIG. 6 is a side view, partially in section, illustrating a method of securing an embodiment of the invention in place within the ear canal of a patient.

FIGS. 4-6, inclusive, illustrate a preferred embodiment and manner of utilizing a structure such as fluid-flow structure 36. In general terms, this preferred structure includes an elongate tubular and malleable body 36a which is either formed with, or provided with, a removably attachable, outer trocar end 36b having the evident sharpened structure which permits selective piercing and penetration of the tympanic membrane as is illustrated in FIG. 5. Leading to the trocar is a compliant, easily bendable tube designed to absorb noise and shock imparted inadvertently from the body portion. Malleability in the body enables changeable formation of the bend in the body to accommodate appropriate positioning of trocar end 36b when device 36 is anchored to frame structure 22.

Suitably provided on body 36a, at a location which is somewhat distant from the trocar equipped end of the device, is an enlargement which provides what is referred to herein as a manipulation bead 36c that permits digital manipulation conveniently of this device during insertion, and during stabilization while readying and applying fixation molding material, or other fixating material, such as is illustrated in FIGS. 5 and 6. Just on the opposite side of bead 34c is an appropriate connector 36d which permits connection of one or more appropriately provided fluid lumens within body 36a to a suitable source and reservoir for delivery and return of fluid. For example, a delivery lumen might be connected to the source of a particular liquid drug which is intended to be delivered into the ear during a vestibular-examination procedure.

Figure 7:
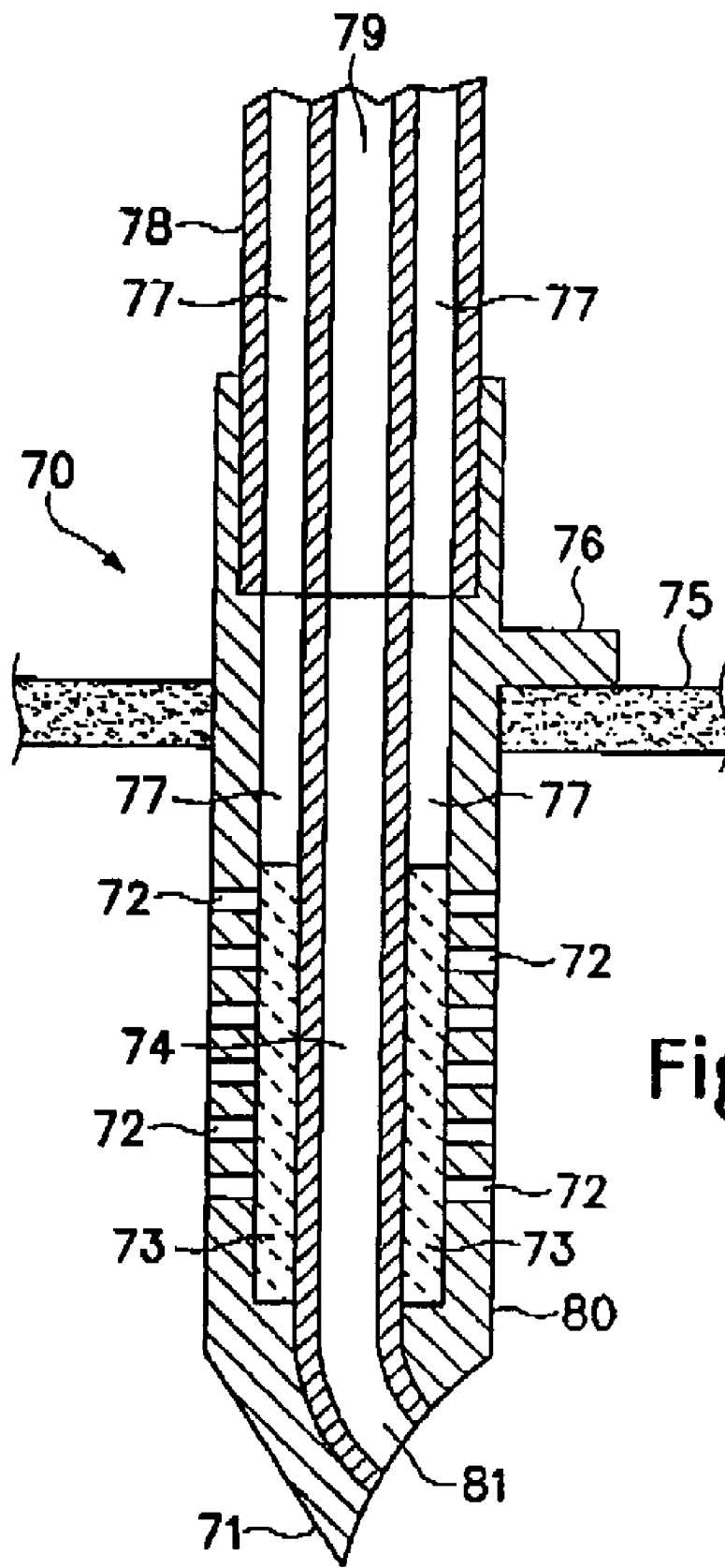
FIG. 7 is an enlarged side sectional view of an embodiment of the invention.

A design with various preferred features is illustrated in FIG. 7. In FIG. 7, device 70 includes needle 80 having tip 71 and fluid outlet 81. Fluid outlet 81 is in fluid communication with bore 74, which in turn is in fluid communication with lumen 79 of catheter 78. Fluids are delivered to the middle ear through lumen 79, central bore 74 and outlet 81. Needle 80 further includes multiple inlets 72, through which fluids can be withdrawn from the middle ear. Withdrawn fluids are drawn past optional filters 73 into lumen 77 within catheter 78. As shown, lumens 77 and 79 are arranged coaxially. Device 70 further includes positioning tab 76 which, when the device is inserted, will contact tympanic membrane 75 and act as a stop, helping to locate the device in its correct position.

Figure 10A:
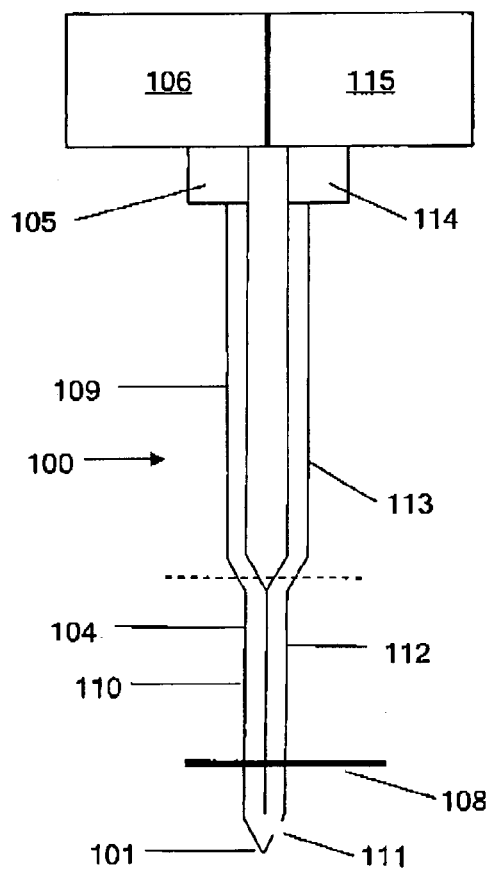
FIGS. 10A and 10B are enlarged side sectional views of embodiments of the invention.
Figure 10B:
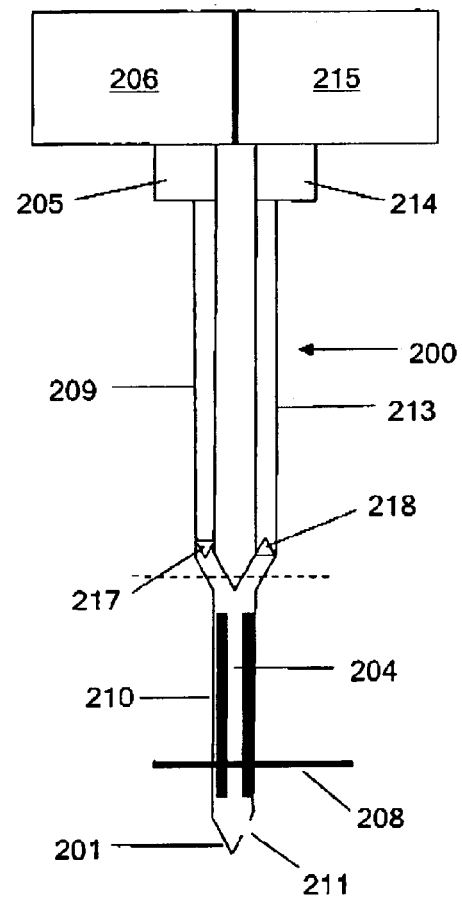

Alternate embodiments of the invention are illustrated in FIGS. 10A and 10B. In FIG. 10A, a two-lumen needle design is shown. Device 100 includes needle 110 having sharpened tip 101 with fluid outlet/inlet 111. Needle 110 is shown inserted through tympanic membrane 108. Needle 110 includes bores 104 and 112, one (bore 104) of which serves as a conduit for delivery of fluids to the middle ear and the other (bore 112) of which serves as a conduit for removal of fluids from the middle ear. Bores 104 and 112 are in fluid communication with lumens 109 and 113, respectively. As shown, lumen 109 is in fluid communication with fluid reservoir 106 via pump 105. Pump 105 controls the delivery of fluids into the middle ear through needle 110, and prevents the undesired return of fluids through bore 104 and lumen 109. Similarly, lumen 113 is in fluid communication with spent fluid reservoir 115 via pump 114. Pump 114 controls the extraction of fluids from the middle ear via needle 110.

In FIG. 10B, a single-lumen needle design is shown. Device 200 includes needle 210 having sharpened tip 201 with fluid outlet/inlet 211. Needle 210 is shown inserted through tympanic membrane 208. Needle 210 includes a single bore 204 which serves as a conduit for delivery of fluids to the middle ear and as a conduit for removal of fluids from the middle ear. Bore 204 in fluid communication with lumens 209 and 213. As shown, lumen 209 is in fluid communication with fluid reservoir 206 via pump 205. Pump 205 controls the delivery of fluids into the middle ear through needle 210. Unidirectional valve 217 prevents the undesired return of fluids through lumen 209. Similarly, lumen 213 is in fluid communication with spent fluid reservoir 215 via pump 214. Pump 214 controls the extraction of fluids from the middle ear via needle 210. Unidirectional valve 218 prevents the return of spent fluid to the middle ear through lumen 213.

A suitable pump is an off-the-shelf drug delivery pump, such as a Disetronic pump, to set, control and adjust drug dosing in the office as indicated by the physician. Throughout the dosing period, if indicated, subject status may be monitored by staff or, alternatively, a head-mounted positional management (HPM) system such as is described in U.S. Pat. No. 6,800,062.

When the invention is used, the tympanic cavity behind the tympanic membrane can act as a circulation reservoir where there is an alternating or pulsating inflow of fresh perfusate and outflow of spent perfusate, thus maintaining the perfusate (solute) concentration that contacts the round window membrane at consistent and optimal levels during the period of perfusion. Thus, this invention allows for a more idealized infusion regime, whereby greater concentrations of a drug can be supplied to the inner ear via a frequent replacement or replenishing of the drug. Fresh perfusate containing a relatively high concentration of the active substances is supplied to the middle ear through the device, where it mixes with spent perfusate, thereby enriching the supply of active substance in the ear. A portion of the spent perfusate is then removed as described. In this way, the concentration of active substance can be maintained at a high level in the middle ear, increasing the rate of absorption. The frequent replenishing of the concentration will result in a much more rapid delivery of the active substance to the inner ear. With this sustained perfusion, the concentration of the drug contacting the round window membrane can be maintained and stabilized at a desired level. This reduces treatment time, so the patient often can be treated in the office situation with assistance from medical professionals on an outpatient basis, rather than being admitted to a hospital or self-administering infusion at home.

Figure 8:
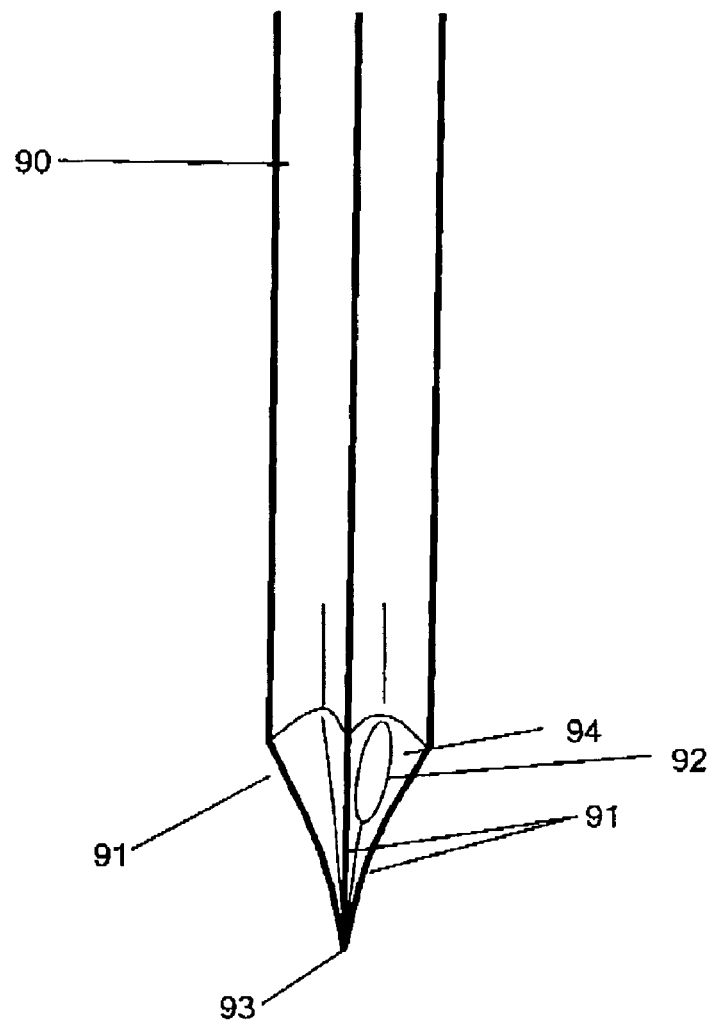
FIG. 8 is an enlarged side view of a preferred needle tip for use with the invention.

A preferred needle design is illustrated in FIG. 8. Needle 90 includes multiple prongs 91 that converge at center point 92. As shown in FIG. 8, needle 90 includes three prongs 91, but a greater number of prongs, such as from 3 to 8 prongs, can be used. The prongs define multiple faces 94 at the tip of needle 91. Fluid outlet 92 extends through one of these faces in the embodiment shown, but it is possible for bore 92 to be placed above the needle tip, so long as it is located within the middle ear when the needle is inserted.

A multicuspid needle tip as shown in FIG. 8 creates multiple incisions extending outward from a central point, thereby forming a corresponding number of skin flaps. These skin flaps are pushed aside upon insertion of the trocar tip through the tympanic membrane. When the trocar tip is removed, these skin flaps can move back into place, thus minimizing healing time, patient discomfort and complications.

As can be seen in FIGS. 5 and 6, a generally illustrated procedure for use of device 36 is shown wherein the trocar end of the device, under the observation of a suitably placed viewing scope 60, is inserted through a slotted speculum 62 into the ear to pierce the tympanic membrane. The slotted speculum 62 is then removed, while still carefully stabilizing the trocar. Following this, and through any suitable device which can eject an appropriate stabilizing and sealing material, the region around body 36a is encapsulated in a flowable and curable sealing substance 64 of any suitable variety, thus to provide local stabilization between the position of the device and the immediately adjacent ear structure. In a preferred embodiment, the device contains external (to the tympanic membrane when inserted) ribs 36e that allow the fixation material to keep the insertion system securely in place after installation and during drug delivery. An inert fixation material, such a curable silicone wax, can be inserted in and around the ear canal and upon solidification fix the trocar and its tubing in place in the external canal, and to seal the canal from possible fluid leakage during the drug delivery procedure.

Manipulation of the device during insertion into the ear and sealing in place, as is illustrated in FIG. 6, is accommodated by digital manipulation utilizing bead 36c while the hand is stabilized against the head.

Figure 9:
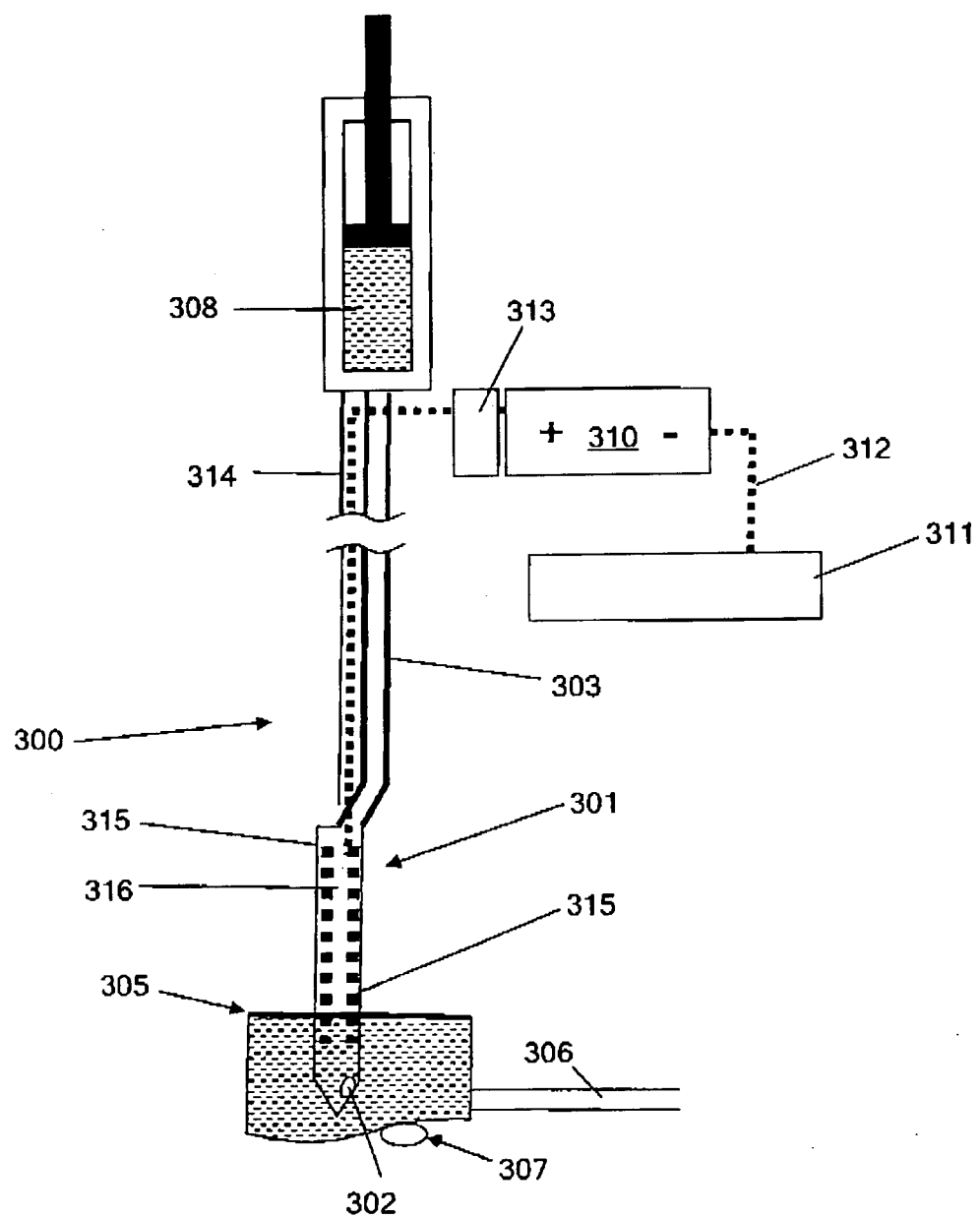
FIG. 9 is a side schematic view of an embodiment of the invention.

FIG. 9 illustrates yet another embodiment of the invention, in which iontophoresis can be applied with the delivery of fluids to the middle ear. Device 300 includes needle 301 having, in the embodiment shown, a single bore 316, which is in fluid communication with fluid outlet 302 and lumen 303. Lumen 303 is in fluid communication with fluid reservoir 308, which in this embodiment is shown as a simple syringe. Pumps and valves can be used in connection with this embodiment of the invention, in the general manner described before (see FIGS. 10A and 10B, for example). Device 300 is shown in FIG. 9 inserted in its proper position with needle 301 penetrating tympanic membrane 305 so fluid outlet 302 resides within the middle ear. The round window membrane is shown schematically at 307 and the Eustachian tube is shown schematically at 306.

In this embodiment, the exterior surfaces of needle 301 are preferably made of a non-conductive material. Within bore 316 of needle 301 resides electroconductive material 315, which is in electrical communication with one (typically the positive) electrode of electrical power source 310 via circuit 314, and is also in contact with fluid residing in bore 316 of needle 301. Circuit 414 and lumen 403 are generally retained within a single catheter. The other (typically the negative) electrode of electrical power source 310 is in electrical communication with body electrode 311, which during operation is applied to the skin of the patient. As shown, a controller 313 controls operation of the electrical power supply to device 300. Iontophoresis is applied though the single-lumen catheter via an electrode that contacts the fluid in the lumen of the needle. The needle in this case is non-metalic and non-conductive on the outside, but conductivity is supplied to the inside. The oppositely charged (typically negative) electrode is applied to the skin. The applied and controlled current forms positively charged ions within the active substance. The round window membrane becomes oppositely charged, thereby attracting the positively charged ions and facilitating their transport to and through the round window membrane. As this is taking place, the perfusate ions are constantly replenished via the catheter, and the spent fluid can pass through the Eustachian tube (ET).

Figure 11:
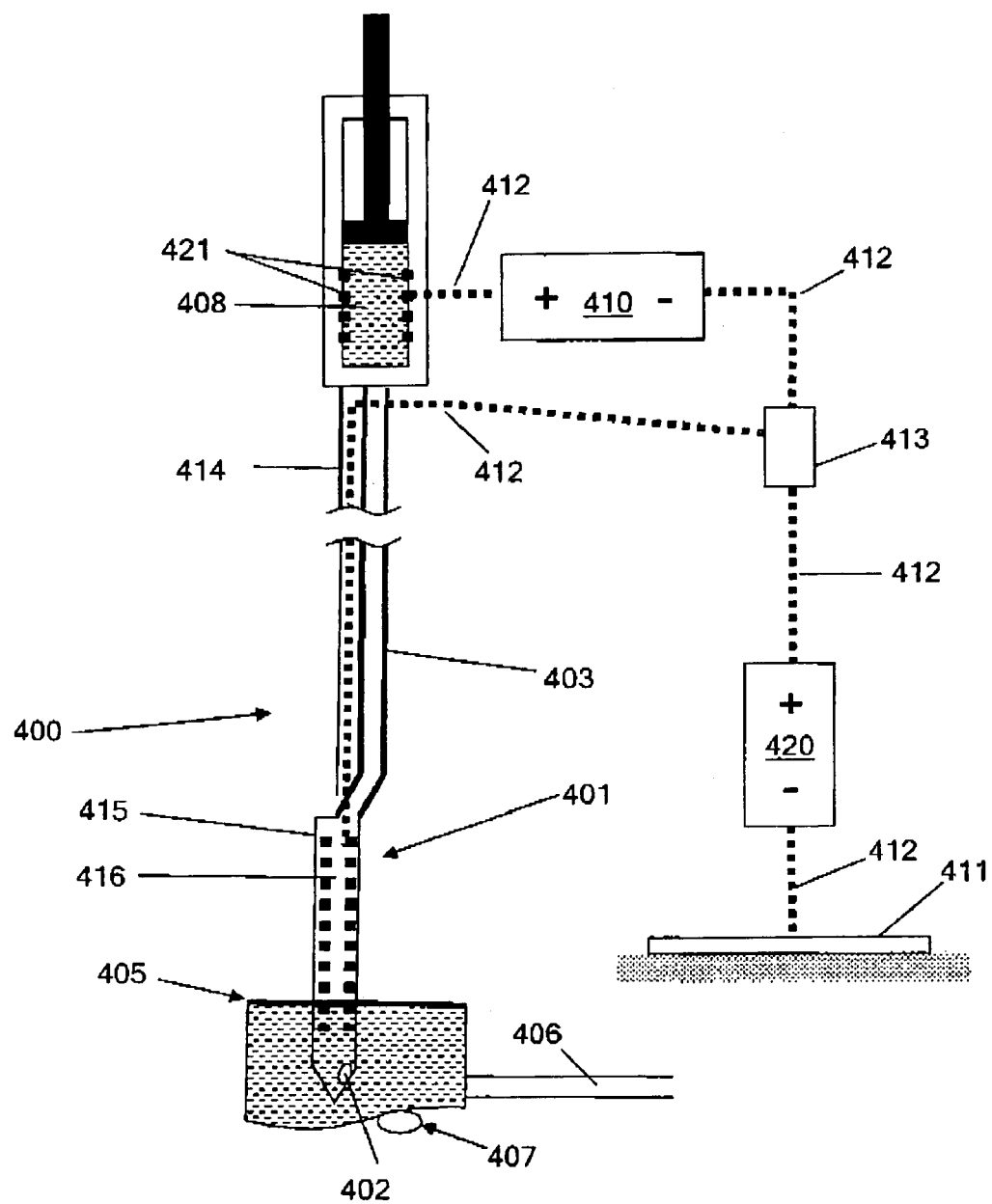
FIG. 11 is a side schematic view of an embodiment of the invention.

FIG. 11 illustrates another embodiment of the invention in which iontophoresis can be applied with the delivery of fluids to the middle ear. Device 400 includes needle 401 having, in the embodiment shown, a single bore 416, which is in fluid communication with fluid outlet 402 and lumen 403. Lumen 403 is in fluid communication with fluid reservoir 408, which in this embodiment is shown as a simple syringe. Pumps and valves can be used in connection with this embodiment of the invention, in the general manner described before (see FIGS. 10A and 10B, for example). Device 400 is shown in FIG. 11 inserted in its proper position with needle 401 penetrating tympanic membrane 405 so fluid outlet 402 resides within the inner ear. The round window membrane is shown schematically at 407 and the Eustachian tube is shown schematically at 406.

In this embodiment, ionizing current is supplied in two stages, first within fluid reservoir 408 and again within needle 401. Ionizing current is supplied to needle 401 in the same manner as described with respect to the embodiment shown in FIG. 9. Electroconductive material 415 resides within bore 416 of needle 401 and is in electrical communication with one (typically the positive) electrode of electrical power source 420 via circuit 412 and 414, and is also in contact with fluid residing in bore 416 of needle 401. Circuit 414 and lumen 403 are generally retained within a single catheter. In this embodiment, ionizing current is also supplied to fluid within fluid reservoir 408 through electrodes 421, which are in electrical communication with electrical power source 410 via circuit 412. As shown, both electrical power source 410 and 420 are controlled through a single controller 413, but multiple controllers can be used if desired. Alternatively, a single electrical power source may provide current to both electrodes 421 and electroconductive material 415. As before, the other (typically the negative) electrode of an electrical power source (either 410 or 420, or both) is in electrical communication with body electrode 411 via circuitry 412, which during operation is applied to the skin of the patient. Iontophoresis is applied to the fluid through both electrodes 421 and electroconductive materials 415. As before, needle 401 is non-metallic and non-conductive on the outside, but conductivity is supplied to the inside. The round window membrane becomes oppositely charged, thereby attracting the positively charged ions and facilitating their transport to and through the round window membrane. By this means, the perfusate ions are constantly replenished to the port structure end of the catheter from the reservoir 408 by the induced passage of drug ions via the catheter, due to the electrodes in the reservoir and within the port structure, and are then attracted to the round window due to the body electrode. Thus, the passage of fluid into the middle ear from the device in this embodiment mainly acts to maintain the continuity of the fluid so that ions can pass, via the catheter and port structure, from the reservoir to the inner ear. Excess fluid can pass from the middle ear through the Eustachian tube (ET).

Although FIG. 11 describes a two-stage iontophoretic device, the device may contain any number of electrodes to create any desired number of stages. The multiple stages desirably create a voltage drop sequentially toward the middle ear.

The embodiments illustrated in FIGS. 9 and 11 each can be modified in various ways. The needle point may be a multicuspid type as described herein. A dual-bore needle as described in FIGS. 7 and 10A may be used, together if desired with an associated lumen and optional pump and/or reservoir to permit spent perfusate to be removed through the needle as described before. Such an embodiment permits alternating supply of fresh perfusate and withdrawal of spent perfusate as described before. A single bore needle can also be used with the embodiment illustrated in FIG. 9, in which the needle is adapted to permit the supply of fresh perfusate and withdrawal of spend perfusate. For example, a single bore needle may be used in combination with a lumen and optional pump and/or reservoir in a manner analogous to the embodiment shown in FIG. 10B.

The device of the invention typically will require only a brief in-office procedure under topical anesthesia for placement in the ear. The device will make a minimal incision in the tympanic membrane that can heal in significantly less time than with existing methods. The device of the invention is designed to remain in the ear for a period of minutes to hours depending on the application, with delivery of the drug or other fluid at a set dosing rate and pattern.

As is generally illustrated in FIG. 1 in the drawings, an appropriate way of anchoring a device 34 or a device 36 to frame structure 22 may be some suitable form of releasable clamp mechanism which allows snap fitting of a region of the tubular bodies in these two devices to the outer side, or sides, of band 26 in the frame structure. Again, the specific manner of anchoring attachment and stabilization are matters of user choice.

What is claimed is:

1. An intra-tympanic apparatus comprising:
   a needle having a sharpened end adapted to pierce the tympanic membrane of an ear and having an opposite end, the needle having at least two longitudinal bores, each in fluid communication with a fluid outlet proximate to the sharpened end and each in fluid communication with a fluid inlet proximate to the opposite end, the fluid outlet being laterally offset from a relatively central longitudinal axis of at least one longitudinal bore with which the fluid outlet is in fluid communication and configured to deliver relative to a central longitudinal axis of the needle a relatively unidirectional angular fluid stream into a middle ear;
   at least two flexible lumens each in fluid communication with the fluid inlet of one of the longitudinal bores of the needle;
   means for delivering a controllable amount of a fluid into the middle ear through at least one of the flexible lumens and the needle; and
   means for removing fluids from the middle ear through the needle.

2. The apparatus of claim 1, wherein the fluid is a drug.

3. The apparatus of claim 1, further comprising storage means for accepting fluid removed from the middle ear.

4. The apparatus of claim 1, further comprising a handle mounted onto at least one of the flexible lumens.

5. The apparatus of claim 4, wherein the handle includes means for moving the needle relative to the handle for insertion and/or retraction of the needle.

6. The apparatus of claim 5, wherein said means for moving the needle is a manipulation bead.

7. The apparatus of claim 1, wherein the sharpened end of the needle is adapted to form multiple connected incisions in the tympanic membrane that extend radially from a central point to form multiple flaps in the tympanic membrane.

8. The apparatus of claim 7, wherein the sharpened end of the needle includes multiple prongs that meet at a center point.

9. The apparatus of claim 1, wherein the needle includes at least one positioning tab for engaging the tympanic membrane when the needle is properly positioned.

10. The apparatus of claim 1, wherein the needle includes one or more external ribs, which reside within the outer ear when the apparatus is properly positioned with the sharpened end within the middle ear.

11. A process for delivering fluid to or removing fluid from the middle ear, comprising a) puncturing a tympanic membrane of an ear with the needle of an apparatus of claim 1, b) securing the needle in place such that the sharpened end and the fluid outlet extend into the middle ear and at least a portion of at least one of a plurality of flexible lumens extends outwardly from the tympanic membrane; and c) delivering at least one fluid to or removing at least one fluid from the middle ear through at least one of a plurality of fluid outlets of the needle.

12. The process of claim 11, wherein the needle is secured in place with a stabilizing and sealing material.

13. The apparatus of claim 1, wherein at least one of the at least two longitudinal bores is configured to remove fluid from the middle ear and at least another of the at least two longitudinal bores is configured to deliver fluid to the middle ear.

14. The apparatus of claim 1, wherein to means for removing fluids from the middle ear comprises at least one spent fluid inlet proximate the sharpened end and configured to withdraw spent fluids from the middle ear, wherein the at least one spent fluid inlet is in fluid communication with at least one of the at least two longitudinal bores.

15. The apparatus of claim 14, further comprising:
   one or more filter structures disposed in a fluid flow path from the at least one spent fluid inlet and configured to filter spent fluid withdrawn from the middle ear by the at least one spent fluid inlet.

* * * * *

UNITED STATES PATENT AND TRADEMARK OFFICE
CERTIFICATE OF CORRECTION

PATENT NO. : 7,351,246 B2 Page 1 of 1
APPLICATION NO. : 11/039556
DATED : April 1, 2008
INVENTOR(S) : John M. Epley It is certified that error appears in the above-identified patent and that said Letters Patent is hereby corrected as shown below:

Column 12, line 14, "comprising a)" should be changed to --comprising:-- and the line starting with --a)-- should be moved one line down.

Column 12, line 30, "wherein to means" should be changed to --wherein the means--.

Signed and Sealed this

First Day of July, 2008

JON W. DUDAS
*Director of the United States Patent and Trademark Office*